United States Patent
Thome et al.

(12)

(10) Patent No.: US 6,340,785 B1
(45) Date of Patent: Jan. 22, 2002

(54) INBRED TOMATO LINE FDR 26-682

(76) Inventors: Cathy R. Thome, 764 Carr Ave., Aromas, CA (US) 95004; Robert F. Heisey, 800 Carignane Dr., Gilroy, CA (US) 95020

(*) Notice: Subject to any disclaimer, the term of this patent is extended or adjusted under 35 U.S.C. 154(b) by 0 days.

(21) Appl. No.: 09/365,366

(22) Filed: Jul. 30, 1999

(51) Int. Cl.[7] .............................. A01H 5/00; A01H 1/00; A01H 1/02; C12N 5/00; C12N 5/02
(52) U.S. Cl. ..................... 800/317.4; 800/317; 800/260; 800/268; 435/423; 435/430
(58) Field of Search .............................. 800/317.4, 317, 800/260, 268; 435/423, 430

(56) References Cited

U.S. PATENT DOCUMENTS 4,843,186 A * 6/1989 Nahum ........................... 800/1

* cited by examiner

*Primary Examiner*—Bruce R. Campell
*Assistant Examiner*—Anne Marie Grunberg
(74) *Attorney, Agent, or Firm*—Gardner, Carton & Douglas

(57) ABSTRACT

The present invention relates to an inbred tomato line, designated FDR 26-682. This invention further relates to plants and seeds of inbred tomato line FDR 26-682 and methods for producing a tomato plant produced by crossing the inbred line FDR 26-682 with itself or another tomato plant possessing commercially desirable characteristics.

12 Claims, No Drawings

INBRED TOMATO LINE FDR 26-682

TECHNICAL FIELD OF THE INVENTION

The present invention relates to a distinctive inbred line of tomato (*Lycopersicon esculentum*) which provides good quality fruit and high yield when used in hybrid combinations.

BACKGROUND OF THE INVENTION

The goal of plant breeding is to develop new, unique and superior varieties. Theoretically, a breeder can generate billions of different genetic combinations via crossing, selfing and selection. A breeder has no direct control at the cellular level. Therefore, two breeders will never develop the same line, or even very similar lines, having precisely the same traits. Descriptions of breeding methods that are commonly used for different traits and crops can be found in one of several reference books (e.g., Allard, R. W., (1960) *Principles of Plant Breeding;* Simmonds, N. W., (1979) *Principles of Crop Improvement;* Sneep, J. et al., (1979) *Plant Breeding Perspectives;* Fehr, (1987) *Principles of Cultivar Development—Theory and Technique*).

The method chosen for breeding or selection depends on the mode of plant reproduction, the heritability of the trait(s) being improved, and the type of variety used commercially (e.g. $F_1$ hybrid, or an open-pollinated variety). The complexity of the inheritance influences the choice of breeding method. One simple method of identifying a superior plant is to observe its performance relative to other experimental plants or to a widely grown standard variety, or to observe its performance in hybrid combinations with other plants. If single observations are inconclusive for establishing distinctness, observations in multiple locations and seasons provide a better estimate of its genetic worth. Proper testing and evaluation should detect any major faults and establish the level of superiority or improvement over current varieties.

The development of commercial tomato hybrids requires the development of homozygous inbred parental lines. In breeding programs desirable traits from two or more breeding lines from various sources or gene pools are combined to develop superior breeding lines. Desirable inbred or parent lines are developed by continuous selfing and selection of the best breeding lines, sometimes utilizing molecular markers to speed up the selection process.

Once the inbred lines that give the best hybrid performance have been identified, the hybrid seed can be produced indefinitely, as long as the homogeneity of the inbred parents is maintained. A single-cross hybrid is produced when two inbred lines are crossed to produce the $F_1$ progeny. Much of the hybrid vigor exhibited by $F_1$ hybrids is lost in the next generation ($F_2$). Consequently, seed from hybrid varieties is not used for planting stock.

There are numerous steps involved in the breeding and development of any new and novel, desirable inbred line with superior combining ability. Plant breeding begins with the analysis and definition of problems and weaknesses of the current germplasm, the establishment of program goals, and definition of specific breeding objectives. The next step is selection of germplasm that possess the traits to meet the program goals and the definition of the best breeding method to reach those goals. The objective is to combine in a single variety or hybrid an improved combination of desirable traits from the parental germplasm. Important characteristics may include higher yield, better flavor, improved color and field holding ability, resistance to diseases and insects, tolerance to drought and heat, along with characteristics related to hybrid seed yields to facilitate the cost of hybrid seed production.

Tomato is a very important crop in all continents of the world. Several plant species associated with the Solanum family have been familiar to mankind since ancient times, and are of great agricultural importance. Solanum species have a general adaptation to variable climatic growing conditions. Tomato (*Lycopersicon esculentum*) is adapted to warm summer growing conditions and for winter growing conditions in warmer or tropical locations or in heated greenhouses. The introduction of hybrid varieties in the 1950's provided a magnitude of benefits like increased yield, better holding ability, adaptation to expanded growing seasons through the use of protected cultivation and improved disease resistance, which resulted in large-scale production of tomato as a commercial crop. The goal in tomato breeding is to make continued improvement in hybrid tomato yields, in horticultural and quality characteristics in order to meet continuous demands for better tomato varieties in developed and emerging world economies.

Tomato (*Lycopersicon esculentum* L.) belongs to the Solaneaceous family. All varieties in the species *esculentum* are self-pollinating. Most other species in the genus Lycopersicon are cross-pollinating. Cross-pollination is affected by insect vectors, most commonly by the honey- or bumblebees. Tomato, like most other Lycopersicon species, is highly variable. Variability in populations is desired for wide adaptation and survival.

SUMMARY OF THE INVENTION

The present invention relates to an inbred fresh market tomato line, designated FDR 26-682. Inbred tomato line FDR 26-682 possesses superior characteristics and combining ability, and it provides an excellent parental line in crosses for producing first generation ($F_1$) hybrids, such as, but not limited to, EF 163R. Specifically, the present invention relates to inbred tomato seed designated FDR 26-682 having ATCC Accession Number PTA-3430. The present invention further relates to tomato plants grown from this tomato seed. Additionally, the present invention relates to pollen and ovules from this tomato plant and to an inbred tomato plant having all of the physiological and morphological characteristics of this tomato plant. Moreover, the present invention relates to a tomato plant regenerated from a tissue culture of tissue regenerated from this tomato plant.

The present invention also relates to a method of producing first generation ($F_1$) hybrid tomato seed. The method involves crossing a tomato plant produced by growing inbred tomato seed designated FDR 26-682 having ATCC Accession No. PTA-3430 with a second inbred line of tomato, and then harvesting the resulting $F_1$ seed. The tomato plant grown from the inbred tomato seed designated FDR 26-682 having ATCC Accession No. PTA-3430 may be used as either the female or male parent.

The present invention also relates to a first generation $F_1$ hybrid tomato plant that is produced by growing the hybrid tomato seed produced by the above-described method and to seed producing by this hybrid tomato plant.

Finally, the present invention also relates to tomato plants having within their pedigree tomato inbred line FDR 26-682.

DETAILED DESCRIPTION OF THE INVENTION

The present invention relates to an inbred fresh market tomato line designated as FDR 26-682. Inbred tomato line FDR 26-682 possesses superior characteristics and combining ability, and provides an excellent parental line in crosses for producing first generation ($F_1$) hybrids, such as, but not limited to, EF 163R.

Inbred tomato line FDR 26-682 was developed as follows:

In January 1991, fruit was harvested from a single $F_1$ hybrid tomato plant from a farmer's field in Culiacan, Sinaloa Mexico, and seeds were extracted from these fruits. One hundred (100) plants from these $F_2$ seeds were planted in Gustine, Calif. in April 1991 in a plot numbered PC9113264. Twenty-three (23) selections, numbered PC9113264-1 to 23, were made from this one hundred (100) plant population. These twenty-three (23) $F_2$ selections were transplanted in Culiacan, Sinaloa, Mexico in September 1991, in fourteen (14) plant plots per $F_3$ line, and numbered as PC9210243 to PC9210265. Two (2) selections were made from plot number PC9210244 in the field in Culiacan, Sinaloa, Mexico. The seed source used to plant the plot number PC9210244 was PC9113264-2, which was genetically fixed for the ripening inhibiting gene rin (Tigchelaar et al., (1978) *HortScience* 13(5): 508–513). Seed harvested on these two (2) $F_3$ selections were planted in the greenhouse in San Juan Bautista, Calif. in March of 1992 in two (2) twelve (12) plant plots numbered PC 927013 and PC927014. Each plot consisted of six (6) pots, each pot containing two (2) plants. The two (2) plants in each pot were crossed with six (6) different Seminis Vegetable Seeds, Inc. (Saticoy, Calif.) proprietary breeding lines, using a different proprietary male parent line for the two (2) plants in each pot, to make $F_1$ experimental seed. Some flowers on each plant were also self-pollinated to produce $F_5$ seed. Hybrid seeds as well as self-pollinated $F_5$ seed was harvested. The twelve (12) plants of each of the two (2) lines were also classified for potential tobacco mosaic virus (hereinafter "TMV") resistance or susceptibility based on their reaction to the widespread presence of TMV inoculum in the greenhouse. Their $F_5$ progeny was also tested for TMV resistance using suitable testing procedures known in the art (i.e., *Screening Procedure for Tobacco Mosaic Virus*, N. J. Phillips, Asgrow Plant Pathology Center, San Juan Bautista Calif. available from Seminis Vegetable Seeds, Inc., the assignee of the present invention; Cirulli, M & F Cicarese, (1975) *Phytop. Medit.* 14:100–105).

The twelve (12) hybrids were then evaluated in the field in Culiacan, Sinaloa, Mexico during the winter of 1993. Based on the performance of the hybrids and the $F_4/F_5$ lines that were homozygous resistant to TMV, four (4) $F_5$ progeny lines of plants selected in the greenhouse in plot PC927014, which were designated as PC92714-5, -7, -9 and -12, were planted in the field in the summer of 1993 at San Juan Bautista. These lines were planted in plot numbers PC932896 to PC932899. Thereafter, each plant in plots PC932896 to PC932899 was classified for uniform shoulder color (hereinafter "uu") or green shoulder color (hereinafter "GS"), and the seed from the five plants with uniform shoulder color was harvested at the end of the growing season. Five (5) $F_6$ lines uniform for shoulder color selected in plot number PC932899, specifically numbered as PC932899-2uu, -5uu, -6uu, -8uu, and -10uu, were planted in a field in San Juan Bautista in the spring of 1994 as plots numbered PC945013 to PC945017 containing sixty (60) plants each. These lines were evaluated for between-plant uniformity. As the plants were found to be sufficiently uniform for horticultural type within lines and the plants were also found to be uniform between all five (5) plots, a bulk of plots numbered PC945013, 5014, 4015, 5016, and 5017 were harvested to become FDR 26-682. This seed was given lot number PC94M14. Additionally, inbred line FDR 26-682 was used as a seed parent in crosses with a proprietary line of Seminis Vegetable Seeds, Inc. designated "670" to produce the hybrid designated EF 163R.

Inbred line FDR 26-682 has shown uniformity and stability for all traits. It has been self-pollinated and planted for a sufficient number of generations, with careful attention to uniformity of plant type to ensure homozygosity and phenotypic stability. No variant traits have been observed or are expected in FDR 26-682.

Inbred tomato line, FDR 26-682, has the following plant and fruit characteristics:

Plant Characteristics

FDR 26-682 is of medium size, medium vigor, and is determinate with bi-pinnate leaves which are medium green in color. The pedicel is jointed. Furthermore, inbred line FDR 26-682 is homozygous for the I gene, which confers resistance to *Fusarium oxysporum* f. sp. Lycopersici race 1, and Tm2a that confers resistance to TMV strain 0, strain 1, and strain 1–2 (see Bournival, B. L. et al., (1990) *Theoretical and Applied Genetics* 79: 641–645; Scott, J. W. & J. P. Jones, (1991). TGC Report No. 41). In addition, inbred line FDR 26-682 has excellent combining ability for plant type in $F_1$ hybrids. Inbred line FDR 26-682 has been used in crosses with other inbred tomato lines possessing commercially desirable characteristics to produce determinate and indeterminate hybrids.

Fruit Characteristics

Inbred line FDR 26-682 is homozygous for the ripening inhibitor gene (rin) that contributes to extended shelf life of fruit in heterozygous hybrids. Fruit of inbred line FDR 26-682 are light green before maturity with a uniform shoulder color (green shoulder absent), large (about 200 grams), with greater than four locules. The fruit shape is deep oblate. The line is of mid season maturity and provides for the same maturity in hybrid combinations. The fruit color of inbred line FDR 26-682 is yellow as it is homozygous for the rin gene.

As discussed earlier, FDR 26-682 is homozygous for the TM2a gene, the rin gene, and has uniform shoulder color. FDR 26-682 has been shown to have excellent combining ability which provides for a high overall rating.

Hybrid EF 163R

Tomato hybrid EF 163R has very firm, smooth, uniform shouldered, globe to deep oblate very large fruit with excellent interior and exterior color. It is midseason maturity with a moderately vigorous vine, which results in good cover and allows good air circulation. It has disease resistance to Verticillium race 1, Fusarium races 1 and 2, Alternaria stem canker, Gray leaf spot (Stemphyllium), and Tobacco Mosaic Virus races 0, 1, and 1–2.

FDR 26-682 derived hybrid EF 163R is most similar to hybrid BR 84 (which is commercially available from LSL Biotechnologies (Tucson, Ariz.)); however, there are numerous differences between these two (2) hybrids. As shown in the Tables below, EF 163R is larger in size and has much better fruit shape then BR 84. Also, BR 84 possesses green shoulders, which is a commercially undesirable trait. Further differences between hybrid EF 163R and BR 84 as well as other commercially available hybrids are shown in the Tables below.

TABLE 1

Culiacan, Sinaloa, Mexico - transplanted 9/20/95

| Hybrid | Overall Rating | Notes |
|---|---|---|
| FDR 26-682 × Line 670 | 4.5 | TMV resistant, Continuous set, consistently very good |
| Line 670 × Line 684 | 3.5 | Green shoulder |
| EF 49 - Commercial check | 2.5 | Late, low fruit set |

TABLE 2

Culiacan, Sinaloa, Mexico - transplanted 9/18/96

| Hybrid | Overall Rating | Notes |
|---|---|---|
| FDR 26-682 × Line 670 | 5.0 | Excellent yield and size, good firmness |
| Line 680 × FDR 26-682 | 4.5 | Very pretty fruit, excellent firmness, good size |
| Line 703 × FDR 26-682 | 4.0 | Good yield, good size, green shoulder, good firmness |
| BR 84 - Commercial check | 4.0 | Good yield, good size, green shoulder, good firmness |

TABLE 3

Culiacan, Sinaloa, Mexico - transplanted 9/23/97

| Hybrid | Overall Rating | Notes |
|---|---|---|
| FDR 26-682 × Line 670 | 5.0 | Excellent fruit shape and size, medium plant |
| Line 680 × FDR 26-682 | 5.0 | Good plant, good set, size, fruit a little flattened but pretty, nice color, excellent firmness |
| Line 703 × FDR 26-682 | 4.5 | Nice plant, nice set and size, pretty fruit, firm, green shoulder ok |
| BR 284 - Commercial check | 4.0 | Set kind of late |
| BR 449 - Commercial check | 4.0 | Med-large fruit, some nipples; |
| BR 84 - Commercial check | 4.0 | Yellow shoulder, not much fruit size |

TABLE 4

San Quintin, Baja California, Mexico - transplanted 5/30/98

| Hybrid | Overall Rating | Notes |
|---|---|---|
| FDR 26-682 × Line 670 | 5.0 | Best set, size, less plant |
| Line 680 × FDR 26-682 | 4.5 | Fruit are a little small but pretty. Not as firm as expected. |
| Line 703 × FDR 26-682 | 5.0 | Good set and size, less ribby and earlier than field variety, good plant but not too big |
| Thunderbay - commercial check | 4.0 | Dark green shoulder, ribby, some unusual shapes, v. good set and size |

TABLE 5

Culiacan, Sinaloa, Mexico - transplanted 10/30/98

| Hybrid | Overall Rating | Notes |
|---|---|---|
| FDR 26-682 × Line 670 | 5.0 | Best fruit set, size, and smoothness of all varieties; very good firmness. |
| Line 680 × FDR 26-682 | 3.0 | Not enough set, variable size |
| Line 703 × FDR 26-682 | 3.5 | Not too bad for this field; color not good |
| FDR 26-682 × Line 725 | 4.5 | Good fruit set and size to top, good plant, a few nipples on top fruit, uniform size |
| Line 670 × PC988517 | 1.0 | Not enough plant |
| Line 680 × PC988517 | 1.0 | Rough fruit, no size |
| BR 440 - commercial check | 3.0 | Too many nipples, firm |
| BR 449 - commercial check | 3.0 | Big fruit but not enough of them |
| BR 84 - commercial check | 3.0 | Persistent green shoulder, not much fruit set |

BR 84, BR 284, BR 440 and BR 449 are all commercially available from LSL Biotechnologies (Tucson, Ariz.).

EF 49 is commercially available from Seminis Vegetable Seeds, Inc. (Saticoy, Calif.). Thunderbay is commercially available from D. Palmer Seed Company, Inc. (Tucson, Ariz.).

Lines 670, 680, 684, 703, 725 and PC988517 are proprietary lines of Seminis Vegetable Seeds, Inc. (Saticoy, Calif.).

DEPOSIT INFORMATION

Two thousand five hundred (2500) seeds of line FDR 26-682 were deposited on Jun. 5, 2001 with the American Type Culture Collection (ATCC), 10801 University Boulevard, Manassas Va. 20110-2209 and assigned ATCC Deposit Number PTA-3430. This deposit was made in compliance with the Budapest Treaty requirements that the duration of the deposit should be for thirty (30) years from the date of deposit or for five (5) years after the last request for the deposit at the depository or for the enforceable life of a U.S. Patent that matures from this application, whichever is longer. Inbred seeds of line FDR 26-682 will be replenished should it become non-viable at the depository.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. Inbred tomato seed designated FDR 26-682 having ATCC Accession No. PTA-3430.

2. A tomato plant produced by growing the seed of claim 1.

3. Pollen of the plant of claim 2.

4. An ovule of the plant of claim 2.

5. An inbred tomato plant having all the physiological and morphological characteristics of the tomato plant of claim 2.

6. A tomato plant regenerated from a tissue culture of the tomato plant of claim 2, said tomato plant capable of expressing all the physiological and morphological characteristics of the tomato plant of claim 2.

7. A method of producing first generation ($F_1$) hybrid tomato seed comprising the steps of crossing a plant of claim 2 with a second inbred line of tomato, and harvesting the resultant $F_1$ seed.

8. The method of claim 7 wherein the said tomato plant of claim 2 is the female parent.

9. The method of claim 7 wherein the said tomato plant of claim 2 is the male parent.

10. A first generation ($F_1$) hybrid tomato plant produced by growing said hybrid tomato seed of claim 7.

11. Seed produced by growing the hybrid plant of claim 10.

12. Tomato plants having within their pedigree tomato inbred line FDR 26-682, wherein said plants have all the morphological and physiological characteristics of inbred line FDR-26-682.

* * * * *

UNITED STATES PATENT AND TRADEMARK OFFICE
CERTIFICATE OF CORRECTION

PATENT NO.   : 6,340,785 B1
DATED        : January 22, 2002
INVENTOR(S)  : Cathy R. Thome and Robert F. Heisey It is certified that error appears in the above-identified patent and that said Letters Patent is hereby corrected as shown below:

<u>Title page,</u>
Item [73], Assignee should read as follows:

-- [73]  Assignee: Seminis Vegetable Seeds, Inc. Saticoy, CA (US) --

Signed and Sealed this

Seventeenth Day of September, 2002

*Attest:*

JAMES E. ROGAN
*Attesting Officer*   *Director of the United States Patent and Trademark Office*